United States Patent [19]

Walter

[11] 4,390,343
[45] Jun. 28, 1983

[54] MULTILAYER ANALYTICAL ELEMENT HAVING AN IMPERMEABLE RADIATION DIFFUSING AND BLOCKING LAYER

[75] Inventor: Bert Walter, South Bend, Ind.

[73] Assignee: Miles Laboratories, Inc., Elkhart, Ind.

[21] Appl. No.: 369,632

[22] Filed: Apr. 19, 1982

Related U.S. Application Data

[63] Continuation-in-part of Ser. No. 280,805, Jul. 6, 1981, abandoned.

[51] Int. Cl.³ .................. G01N 33/52; G01N 33/54
[52] U.S. Cl. ................................. 436/518; 422/56; 422/57; 427/2; 435/7; 435/805; 436/170; 436/810
[58] Field of Search ............... 23/230 B, 915; 422/56, 422/57, 58, 55; 435/7, 805; 424/12; 427/2

[56] References Cited

U.S. PATENT DOCUMENTS

| | | | |
|---|---|---|---|
| 3,654,179 | 4/1972 | Bauer | 422/56 X |
| 3,992,158 | 11/1976 | Przybylowicz et al. | 422/57 |
| 4,042,335 | 8/1977 | Clement | 422/56 |
| 4,050,898 | 9/1977 | Goffe et al. | 422/57 |
| 4,066,403 | 1/1978 | Bruschi | 422/57 X |
| 4,144,306 | 5/1979 | Figueras | 422/56 |
| 4,166,093 | 8/1979 | Smith-Lewis et al. | 422/56 |
| 4,168,146 | 9/1979 | Grubb et al. | 422/56 X |
| 4,258,001 | 3/1981 | Pierce et al. | 422/56 X |
| 4,318,709 | 3/1982 | Falb et al. | 422/56 X |

*Primary Examiner*—Arnold Turk
*Attorney, Agent, or Firm*—Roger N. Coe

[57] ABSTRACT

A multilayer analytical element for detecting a ligand in or the ligand binding capacity of a liquid sample of the type having a reagent layer incorporating reagents which are responsive to the ligand in or the ligand binding capacity of the sample to give a detectable response, a radiation diffusing and blocking layer, and a support layer, the improvement wherein the radiation diffusing and blocking layer is (a) interposed between the reagent layer and the support layer; (b) impermeable to the ligand, reagents of the reagent layer, and products of their interreaction; and (c) inert to the ligand, reagents of the reagent layer, and products of their interreaction.

29 Claims, 6 Drawing Figures

MULTILAYER ANALYTICAL ELEMENT HAVING AN IMPERMEABLE RADIATION DIFFUSING AND BLOCKING LAYER

RELATED APPLICATION

The present application is a continuation-in-part of Ser. No. 280,805, filed July 6, 1981, now abandoned.

BACKGROUND OF THE INVENTION

1. Field of the Invention

The present invention relates to the field of analytical test elements and methods, such as are useful in manual and automated diagnostic systems, and, more particularly, to multilayer analytical elements useful in the qualitative and quantitative determination of body fluid constituents and medicaments present in such body fluids.

2. Brief Description of the Prior Art

Test devices in the form of test strips and similar solid state analytical elements have become commonplace in the analysis of various types of samples, particularly biological fluids. Test strips designed for detecting clinically significant substances in biological fluids, such as serum and urine, have been advantageous in the diagnosis of disease.

Test strips of various types have been known and used for many years in a wide variety of fields, from the most familiar pH test paper devices to in vitro dignostic devices for the detection of various urine and blood components such as glucose, protein, occult blood and so forth (e.g., as described in U.S. Pat. Nos. 3,164,534; 3,485,587; and 3,012,976). Reagent compositions found in such test strips, often having limited sensitivity, interact with the constituent or constituents to be determined by direct chemical reaction and are applied to the detection of substances that are present in liquid samples at concentrations in the millimolar range or above.

(a) Multilayer Analytical Elements

A basic multilayer integral analytical element is described in U.S. Pat. No. 3,092,465. Such multilayer elements use an absorbent firbrous carrier impregnated with one or more reagents, typically including a color former, over which is coated a semi-permeable membrane. Upon contact with a test liquid, analyte passes through the membrane and into the fibrous carrier to generate color in an amount related to the concentration of analyte. The membrane prevents passage and absorption of certain interfering components such as red blood cells, that could impair accurate reading of the color provided as a test result.

Other multilayer integral analytical elements are described in U.S. Pat. No. 3,992,158. Such elements can receive a liquid sample and spread the sample within a spreading layer of the element to obtain in the element an apparent uniform concentration of analyte, other appropriate sample constituent or analyte product and produce in the presence of analyte an analytical result that can be measured quantitatively by automated devices, using techniques such as spectrophotometry, fluorimetry, etc. Such elements can include spreading layers and reagent layers that contain a reactive or otherwise interactive material that, by virtue of its activity, promotes in the element a radiometrically detectable change, such as a color change.

U.S. Pat. No. 4,042,355 relates to an element having (1) a reagent layer which reacts with the analyte to form a diffusible, detectable species; (2) a nonfibrous radiation blocking layer, permeable to the detectable species and having an opacifying agent; and (3) a nonfibrous, radiation-transmissive registration layer in which the detectable species is detected. The element is, thus, read from below.

U.S. Pat. No. 4,066,403 (Re 30,267) relates to an element including () a reagent which reacts with the analyte to produce a decomposition product; and (2) a reagent which reacts with the decomposition product or an intermediate to provide a detectable change, and having, as an improvement, a barrier composition separating reagent (1) from reagent (2), and being substantially uniformly permeable to the decomposition product and substantially impermeable to interferants. Therefore, what this does is add a "filtering" layer between the "reagent" layer and the "registration" layer.

U.S. Pat. No. 4,144,306 relates to an element in which the reagent layer contains a nondiffusible material including a preformed, detectable moiety which is released and becomes diffusible in the presence of the analyte. The registration layer receives the diffusible species. Layers within the element are composed such that the preformed, detectable moiety released from the reagent layer can be detected selectively within the element.

U.S. Pat. No. 4,166,093 relates to an element having (1) a radiation-transmissive reagent layer that reacts with an analyte to provide a detectable species, and (2) a porous radiation-blocking layer which is permeable to the analyte. As an improvement, it also has (3) a radiation-transmissive, detectable species migration-inhibiting layer between the reagent layer and the porous radiation-blocking layer. The migration-inhibiting layer is permeable to the analyte and inhibits the migration of the detectable species to the radiation-blocking layer.

(b) Specific Binding Assay Device

Solid phase test devices have been applied to heterogeneous specific binding assays in attempts to overcome the inconveniences and disadvantages of the requisite separation step. A commonly used solid phase device of this type comprises a nonporous surface, such as the interior surface of a test tube or other vessel, to which antibody is affixed or coated by adsorption or covalent coupling. U.S. Pat. Nos. 3,826,619; 4,001,583; 4,017,597; and 4,105,410 relate to the use of antibody coated test tubes in radioimmunoassays. Solid phase test devices have also been used in heterogeneous enzyme immunoassays (U.S. Pat. Nos. 4,016,043 and 4,147,752) and in heterogeneous fluorescent immunoassays (U.S. Pat. Nos. 4,025,310 and 4,056,724; and British Pat. Spec. No. 1,552,374).

The use of such heterogeneous specific binding assay test devices is exemplified by the method of U.S. Pat. No. 4,135,884 relating to a so-called "gamma stick". The test device is incorporated with the antibody reagent and is brought into contact with the liquid sample and with remaining reagents of the reaction system, principally the label conjugate. After an incubation period, the solid phase device is physically removed from the reaction solution and the label is measured either in the solution or on the test device.

Similar devices where the antibody reagent is entrapped in a matrix such as a gel or paper web are described in U.S. Pat. Nos. 3,925,017; 3,970,429; 4,138,474; 3,966,897; 3,981,981 and 3,888,629 and in German OLS No. 2,241,646. Likewise, devices for use in heterogeneous specific binding assays wherein the antibody reagent is fixed to a matrix held in a flowthrough column are known. (U.S. Pat. Nos. 4,036,947; 4,039,652; 4,059,684; 4,153,675; and 4,166,102). The test device is usually incorporated with less than all of the necessary reagents for carrying out the assay and is merely a means for rendering the necessary separation step more convenient.

Finally, heterogeneous specific binding assay test devices have been described wherein most or all of the necessary reagents are incorporated with the same carrier element, and wherein reagent/sample contacts and separation of the free- and bound-phases are accomplished by capillary migrations along the carrier element (U.S. Pat. Nos. 3,641,235; 4,094,647 and 4,168,146). The devices described in such patents are generally considered difficult to manufacture and susceptible to irreproducibility due to the complex nature of the many chemical and physical interactions that take place along the carrier element during performance of an assay. Yet another approach to a heterogeneous immunoassay element is exemplified by U.S. Ser. No. 973,669, published as European Patent Application 0 013 156.

The application of homogeneous specific binding assay reagent systems to solid state test devices would provide great advantages to the routine user of such assay systems. The determination of ligands appearing in very low concentrations in liquid samples would be simplified to the steps of contacting the device with the sample and measuring, either by visual observation or by instrumental means, the resulting signal. Reagents would be provided in a solid form, with no need to store, dispense or mix liquid reagents as required when using the prior art test kits. Solid state devices would also be much more adaptable to automation than the prior art liquid systems.

British Patent Spec. No. 1,552,607, commonly assigned herewith, describes homogeneous specific binding assay systems employing various novel labels, including chemiluminescent labels, enzyme substrate labels and coenzyme labels. At page 23, line 12 et seq of this patent there is the suggestion to incorporate the assay reagents with various carriers including liquid-holding vessels or insoluble, porous, and preferably absorbent, matrices, fleeces, or flocks; gels; and the like. This lacks a detailed teaching of how to apply homogeneous specific binding assay reagent systems to solid state test devices.

German OLS No. 2,537,275 describes a homogeneous specific binding assay reagent system and poses the possibility of using slides or strips incorporated with antibody in performing the assay. In this suggestion, the label conjugate would first be mixed with the sample and thereafter the antibody incorporated test device contacted with the reaction mixture. After a suitable incubation time, it is proposed that the test device would be rinsed with buffer, dried, and then the signal (fluorescence) measured. Thus, this German OLS poses a test device and assay method much like those already known for heterogeneous specific binding assay techniques wherein the test device is immersed in the liquid reaction mixture, incubated, thereafter removed, washed, and finally read. Additionally, the proposed test device does not incorporate all of the binding assay reagents with the carrier element. Specifically, only the antibody is proposed to be incorporated with the carrier element, the label conjugate being separately added to the sample under assay prior to contact with the proposed test device.

Copending U.S. Ser. No. 255,521, filed on Apr. 20, 1981, and commonly assigned herewith, discloses a method for determining the presence of a ligand in or the ligand binding capacity of a liquid test sample, the method comprising the steps of (1) adding to the liquid sample a label conjugate comprising the ligand, or a binding analogue thereof, chemically bound to a label, (2) contacting the sample with a test device comprising a carrier matrix incorporated with reagents which, when combined with the label conjugate, produce a homogeneous specific binding assay system which produces a detectable response which is a function of the presence of the ligand or the ligand binding capacity, thereby producing the response, and (3) measuring the response.

Copending U.S. Ser. No. 202,378, filed on Oct. 30, 1980, now abandoned, and commonly assigned herewith, discloses a homogeneous specific binding assay device, a method for its preparation, and a method for its use in determining a ligand in or the ligand binding capacity of a liquid sample. This includes, for example, a test device for determining a ligand in or the ligand binding capacity of a liquid sample, comprising (a) reagents for a homogeneous specific binding assay system which produces a detectable response that is a function of the presence of the ligand in or the ligand binding capacity of the sample, and (b) a solid carrier member incorporated with the reagents.

Copending U.S. Ser. No. 253,147, filed on Apr. 10, 1981, and commonly assigned herewith, discloses a homogeneous specific binding assay device for use in determining a ligand in a liquid sample, comprising (a) a reagent composition including a complex of (i) a label conjugate comprising a label component coupled to the ligand or a specific binding analog thereof, and (ii) a specific binding partner for the ligand, the label providing a detectable response, or interacting with a detectant system to provide a detectable response, which is different when the label conjugate is bound by the binding partner compared to when it is not so bound and (b) a carrier incorporated with the complex.

SUMMARY OF THE INVENTION

Problems which exist in prior art elements have been recognized and are avoided or overcome by the multilayer analytical element of the present invention. Blocking layers used in prior art elements are required to be permeable to the ligand, reagents of the reagent layer, or products of their interraction since the response of the element is read from the element surface away from the reagent layer, i.e., the support layer surface.

The problem is that electromagnetic radiation, such as emitted in reflectance and fluorescence systems, is affected by support layers, such as polystyrene or polyester layers, through which it must pass in these prior art elements. A portion of the electromagnetic radiation, such as light, which passes through the support layer is trapped inside the layer. Thus, it acts, in essence, as a fiber optic. As such, the amount of electromagnetic radiation, such as light, which is detected does not precisely indicate the amount resulting from the reaction which has occurred in the element. Dose response results and the like therefore do not entirely represent the amount of electromagnetic radiation from the response to the ligand in the reagent layer. In the case of elements read using fluorescence systems, a constant amount of emitted light is trapped and so this problem has a more pronounced effect on the reliability of results at low ligand concentrations. In the case of elements read using reflectance systems, the problem is more severe at high ligand concentrations.

These problems are avoided or overcome in the multilayer analytical element of the present invention. In having overcome these problems, the element of the invention emits an enhanced electromagnetic response, or signal, as xompared to prior art elements. Even more notably, the ratio of signal radiation (S) to background radiation (B) emitted is enhanced, in that interfering background radiation is avoided, by a factor of at least an order of magnitude ($10\times$), as is demonstrated in the examples, infra.

Thus, in accordance with the present invention, there is provided a multilayer analytical element for detecting a ligand in or the ligand binding capacity of a liquid sample of the type having a reagent layer incorporating reagents which are responsive to the ligand in or the ligand binding capacity of the sample to give a detectable response, a radiation diffusing and blocking layer, and a support layer, the improvement wherein the radiation diffusing and blocking layer is (a) interposed between the reagent layer and the support layer; (b) impermeable to the ligand, reagents of the reagent layer, and products of their interraction; and (c) inert to the ligand, reagents of the reagent layer, and products of their interraction.

DESCRIPTION OF THE PREFERRED EMBODIMENTS

Figure 1:
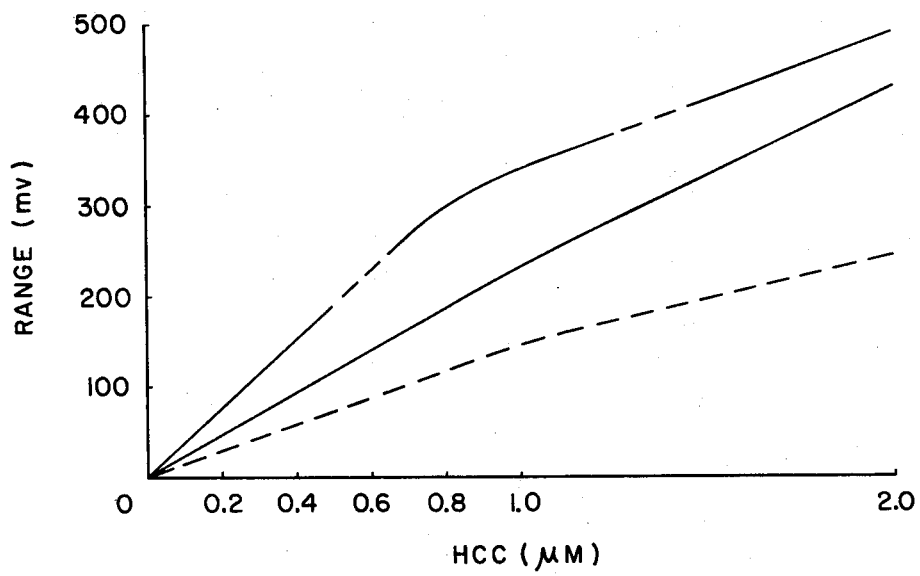
FIGS. 1-2 are graphical representations of data obtained from the experiments described in Example I.

Although specific terms are used in the following description for clarity, they refer only to the particular embodiment of the invention selected for illustration, and do not limit the scope of the invention.

1. Ligand

The term ligand is used to refer to body fluid constituents and medicaments or other substances present in such body fluids. The following exemplifies a number of such possible ligands.

Reagent compositions are known for blood, plasma or serum ligands such as ascorbic acid, bile acids bilirubin, cholesterol, creatinine, glucose, lactic acid, phospholipids, triglycerides, urea nitrogen (BUN) and uric acid. Also important is the determination of blood chemistry enzyme ligands such as amylase, cholinesterase, creatine phosphokinase (CPK), the dehydrogenases (hydroxybutyric, isocitric, lactic and malic), lipase, phenylalanine, the transaminases (glutamic oxaloacetic and glutamic pyruvic), acid and alkaline phosphatases, gamma-glutamyl transpeptidase, leucine aminopeptidase and the erythrocyte enzymes (glucose-6-phosphate dehydrogenase, 6-phosphogluconate dehydrogenase, glutathione reductase and pyrubate kinase). Testing is also possible for blood protein ligands such as albumin, cryoglobins, components of the coagulation and fibrinolytic systems, complement factors and the cellular and serum immune effectors such as interferon and immunoglobins, as is more fully discussed, infra, with reference to homogeneous specific binding assays.

Likewise, reagent compositions are known for urine chemistry determinations. In the field of urine chemistry such ligands generally include ascorbic acid, albumin, creatine, creatinine, glucose, bile acids, bilirubin, protein, ketones, occult blood, nitrite, amylase and phenylpyruvic acid.

The present assay element may also be applied to the detection of any ligand for which there is a specific binding partner and, conversely, to the detection of the capacity of a liquid medium to bind a ligand (usually due to the presence of a binding partner for the ligand in the medium). The ligand usually is a peptide, polypeptide, protein, carbohydrate, glycoprotein, steroid, or other organic molecule for which a specific binding partner exists in biological systems or can be synthesized. The ligand, in functional terms, is usually selected from the group comprising antigens and antibodies thereto; haptens and antibodies thereto; and hormones, vitaminis, metabolites and pharmacological agents, and their receptors and binding substances. Usually, the ligand is an immunologically-active polypeptide or protein or molecular weight between 1,000 and 10,000,000, such as an antibody or antigenic polypeptide or protein, or a hapten of molecular weight between 100 and 1,500.

Representative polypeptide ligands are angiotensin I and II, C-peptide, oxytocin, vasopressin, neurophysin, gastrin, secretin, bradykinnin, and glucagon.

Representative protein ligands include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erthropoietin, transferrin, homopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulated hormone, leutinizing hormone, gonadotropin, thyroid stimulating hormone, placental lactogen, intrinsic factor, transcobalamin, serum enzymes such as alkaline phosphatases, cholinesterase, glutamic oxaloacetic transaminase, glutamic pyruvic transaminase, and uropepsin, endorophins, enkephalins, protamine, tissue antigens, bacterial antigens, and viral antigens such as hepatitis associated antigens (e.g., $HB_sAg$, $HB_cAg$ and $HB_eAg$).

Representative hapten ligands include the general classes of drugs, metabolites, hormones, vitamins, and the like organic compounds. Haptenic hormones, include thyroxine and triiodothyronine. Vitamins include vitamins A, B, e.g., $B_{12}$, C, D, E and K, folic acid and thiamine. Drugs include antibiotics such as aminoglycosides, e.g., gentamicin, tobramycin, amikacin, sisomicin, kanamycin, and netilmicin, penicillin, tetracycline, terramycin, chloromycetin, and actinomycetin; nucleosides and nucleotides such as adenosine diphosphate (ADP), adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxin, and adrenocortical steroids; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, procainamide, N-acetylprocainamide, the amphetamines, the catecholamines, and the antihistamines.

The liquid medium to be assayed can be a naturally occuring or artificially formed liquid suspected to contain the ligand, and usually is a biological fluid or a dilution thereof. Biological fluids that can be assayed include serum, plasma, urine, saliva, and amniotic and cerebrospinal fluids.

2. RADIATION DIFFUSING AND BLOCKING LAYER

The position of the radiation diffusing and blocking layer, relative to the reagent layer(s) and support layer, is critical to the present invention. The characteristics of the radiation diffusing and blocking layer arise from the constituents with which it is prepared and these characteristics are, likewise, critical to the invention.

The radiation blocking layer of the invention is a radiation diffusing and blocking layer which is interposed between the reagent layer(s) and the support layer. It can be in direct contact with one surface of the reagent layer(s); the signal emitted from the reagent layer is then read from the other surface of the reagent layer(s). As such, the radiation signal is not required to pass through any layer or material for detection other than the reagent layer from which it is emitted. When the reagent layer does not bind well to the radiation diffusing and blocking layer it is sometimes possible to treat or activate the surface of the radiation diffusing and blocking layer by suitable treatment, e.g., treatment with sodium hydroxide, to improve the bond achieved between the reagent layer and the radiation diffusing and blocking layer. Alternatively, a subbing layer can be positioned between the radiation diffusing and blocking layer and the reagent layer(s) to improve the bonding or adherence of the reagent layer.

The characteristics or properties of the radiation diffusing and blocking layer are that it is opaque, relatively thin and both impermeable and inert to the ligand, reagents of the reagent layer, and products of their interraction. The radiation diffusing and blocking layer contains a white or light color pigment, preferably uniformily distributed throughout the layer or at least the surface of the layer adjacent to the reagent or subbing layer. More particularly, the radiation diffusing and blocking layer can comprise any radiation impermeable pigment incorporated into any suitable resin or polymeric material which is compatible with the substrate or support material on one hand and with the reagent layer or subbing layer on the other hand. If polymeric in nature, the radiation diffusing and blocking layer may be a homopolymer or a copolymer. The radiation diffusing and blocking layer can be any suitable thickness, but will normally be between about 0.0002 and about 0.02 inches in thickness.

Examples of radiation impermeable pigments which can be used include titanium dioxide, barium sulfate, zinc oxide, magnesium oxide, zirconium dioxide and the like. Normally, the upper limit on the amount of pigment present will be less than 40% solids content and lower limit will be above 2% solids content.

Examples of suitable resins which can be employed for the radiation diffusing and blocking layer are anhydride resins which include methyl vinyl ether-maleic anhydride copolymer; ethylene-maleic anhydride copolymer; octadecengl-1-maleic anhydride copolymer; octadecyl vinyl ether-maleic anhydride copolymer; styrene-maleic anhydride copolymer, and the like.

Examples of other polymeric materials which can be used for the radiation diffusing and blocking layer are polyvinly acetate, polyvinyl methacrylate, polybutadiene, polychoroprene, polyvinylpyrrolidone, and the like.

3. HOMOGENEOUS SPECIFIC BINDING ASSAYS

Reagents for any homogeneous specific binding assay system can be incorporated in the present test device. In general, homogeneous specific binding assay techniques are based on the special interaction between (1) a conjugate of a binding component and a label and (2) a binding partner to the binding component in the conjugate, whereby a characteristic of the label is different when the label conjugate is bound by the binding partner compared to when such conjugate is not so bound. The affected characteristic of the label may be of any measurable nature, for instance, a chemical or physical quality of the label. In some cases, the affected characteristic is a chemical reactivity in a predetermined reaction which involves the formation or breaking of chemical bonds, covalent or noncovalent. In other cases, the affected characteristic is a physical characteristic of the label which can be measured without chemical reaction.

In the majority of cases, the present test device will incorporate homogeneous specific binding assay reagents which interact with the ligand in or its binding capacity of the sample in an immunochemical manner. That is, there will be an antigen-antibody or hapten-antibody relationship between reagents and/or the ligand or its binding capacity in the sample. Such assays therefore are termed immunoassays and the special interaction between the label conjugate and its binding partner is an immunochemical binding. Thus, in such instances, the binding component of the label conjugate is an antigen, hapten or antibody (or a fragment thereof) and the binding partner is its corresponding immunochemical binding partner. However, it is well understood in the art that other binding interactions between the label conjugate and the binding partner serve as the basis of homogeneous specific binding assays, including the binding interactions between hormones, vitamins, metabolites, and pharmacological agents, and their respective receptors and binding substances.

Where the sample is being assayed to determine the presence or amount of a particular ligand therein, the reagents for the homogeneous specific binding assay technique comprise, in the usual case, (1) a label conjugate composed of the ligand, or a binding analog thereof, chemically coupled to the label, (2) a binding partner for the ligand, e.g., an antibody or fragment thereof, a natural receptor protein, and the like, and (3) any ancillary reagents necessary for measuring the labeling substance in the label conjugate. A limiting amount of the binding substance is introduced so that any ligand in the sample will compete with the label conjugate for binding to the binding partner. The distribution of the label between the bound-species and the free-species will therefore determine the magnitude of the detectable response from the label, which in turn will be a function of the presence of the ligand. Another scheme for determining a ligand is presented where the label conjugate is composed of a labeled binding partner of the ligand and upon binding to the ligand the label is affected in terms of its detectable response. Where ligand binding capacity of the sample is under assay, the label conjugate will be composed of the ligand, or a binding analog thereof, chemically coupled to the label whereby the capacity of the sample to bind the label conjugate, such as due to the presence of a binding partner of the ligand in the sample, determines the effect made on the detectable signal from the label.

Several different homogeneous specific binding assay systems are known in the art, and the following are examples, without limiting the scope of the present invention, of some such systems contemplated for use in the present test device. The following systems are listed according to the nature of the label used.

(a) Enzyme Prosthetic Group Labels

In this system, the label is a prosthetic group of an enzyme, and the ability of a catalytically inactive apoenzyme to combine with the prosthetic group label to form an active enzyme (holoenzyme) is affected by binding of the label conjugate with its binding partner. Resulting holoenzyme activity is measurable by conventional detectant system to yield an ultimate detectable signal. Assay systems of this type are described in commonly assigned, copending application Ser. No. 45,423, filed June 4, 1979, now U.S. Pat. No. 4,238,565 (corresponding to published British Patent Spec. No. 2,023,607). A particularly preferred prosthetic group-labeled assay scheme employs flavin adenine dinucleotide (FAD) as the label and apoglucose oxidase as the apoenzyme. Resulting glucose oxidase activity is measurable by a colorimetric detectant system comprising glucose, peroxidase, and an indicator system which produces a color change in response to hydrogen peroxide.

In this preferred assay scheme, the FAD-label conjugate is preferably of the formula:

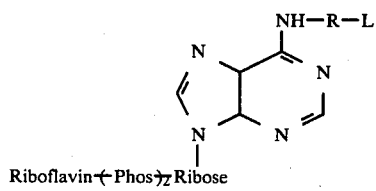

Riboflavin—(Phos)$_2$Ribose wherein Riboflavin—(Phos—)$_2$Ribose represents the riboflavin-pyrophosphate-ribose residue in FAD, R is a linking group, and L is the binding component, e.g., the ligand or analog thereof. An example of such a conjugate is the FAD-theophylline conjugate disclosed in co-pending U.S. Ser. No. 202,378 filed on Oct. 30, 1980, and commonly assigned herewith.

(b) Enzyme Substrate Labels

In this system, the label is selected so that the label conjugate is a substrate for an enzyme and the ability of the enzyme to act on the substrate-label conjugate is affected, either in a positive or negative sense, by binding of the label conjugate with its binding partner. Action of the enzyme on the substrate-label conjugate produces a product that is distinguishable in some feature, usually a chemical or physical feature such as chemical reactivity in an indicator reaction or such as a photometric character, e.g., fluorescence or light absorption (color). Assay systems of this type are described in commonly assigned, copending applications Ser. Nos. 894,836, filed Apr. 10, 1978, now U.S. Pat. No. 4,230,797 (corresponding to published German OLS No. 2,618,511) and 87,819, filed Oct. 23, 1979; now U.S. Pat. No. 4,279,992 and in *Anal. Chem.* 48:1933 (1976), *Anal. Biochem.* 77:55 (1977) and *Clin. Chem.* 23:1402 (1977).

A particularly preferred substrate-labeled assay scheme employs a label conjugate of the substrate

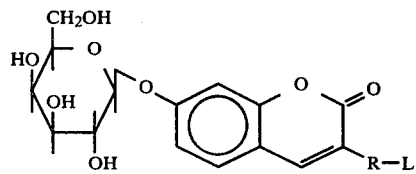

wherein R is a linking group and L is the binding component, e.g., the ligand or analog thereof, whereby the ability of the enzyme β-galactosidase to cleave the conjugate yielding a product distinguishable by its fluorescence is inhibited by binding of the conjugate with its binding partner.

(c) Coenzyme Labels

The label conjugate in this system is composed, in its label portion, of a coenzyme-active functionality, and the ability of such coenzyme label to participate in an enzymatic reaction is affected by binding of the label conjugate with its binding partner. The rate of the resulting enzymatic reaction is measurable by conventional detectant systems to yield an ultimately detectable signal. Assay systems of this type are described in commonly assigned, copending application Ser. No. 894,836, filed Apr. 10, 1978 (corresponding to published German OLS No. 2,618,511); and in *Anal. Biochem.* 72:271 (1976), *Anal. Biochem.* 72:283 (1976) and *Anal. Biochem.* 76:95 (1976).

(d) Enzyme Modulator Labels

The label conjugate in this system is composed, in its label portion, of an enzyme modulating functionality such as an enzyme inhibitor or stimulator, and the ability of such modulator label to modulate the activity of an enzyme is affected by binding of the label conjugate with its binding partner. The rate of the resulting enzymatic reaction is measurable by conventional detectant systems to yield an ultimately detectable signal. Assay systems of this type are described in commonly owned U.S. Pat. No. 4,134,792.

(e) Enzyme Labels

In this system, the label is an enzyme and the activity of the enzyme label is affected by binding of the label conjugate with its binding partner. Resulting enzyme activity is measurable by conventional detectant systems to yield an ultimately detectable signal. Assay systems of this type are described in U.S. Pat. Nos. 3,817,837 and 4,043,872.

(f) Quenchable Fluorescent Labels

The label conjugate in this system is composed, in its label portion, of a fluor the fluorescence of which is quenched in some measurable degree when the label conjugate is bound by its binding partner, usually a protein such as an antibody. The fluorescent label is measured directly, with its fluorescence being the detectable signal. Assay systems of this type are described in U.S. Pat Nos. 4,160,016 and in *J. Clin. Path.* 30:526 (1977).

(g) Fluorescence Polarization Labels

The label in this system is also a fluor; however, the affected characteristic is polarization of fluorescence due to binding of the label conjugate by its binding partner, usually a protein such as an antibody. Assay systems of this type are described in *J. Exp. Med.* 122:1029 (1965).

(h) Chemically-Excited Fluorescent Labels

In this system, the label is again a fluor, however, the ability of the fluor label to be chemically excited to an energy state at which it fluoresces is affected by binding of the label conjugate with its binding partner. Chemical excitation of the label is usually accomplished by exposure of the fluor label to a high energy compound formed in situ. Assay systems of this type are described in commonly-owned copending application Ser. No. 4,580, filed Jan. 18, 1979, now U.S. Pat. No. 4,238,195.

(i) Double Antibody Steric Hindrance Labels

Another assay system is the double antibody immunoassay system described in U.S. Pat. Nos. 3,935,074 and 3,998,943. The label conjugate comprises two epitopes, one of which participates in the immunological reaction with the ligand and antiligand antibody and the other of which is bindable by a second antibody, with the restriction that the two antibodies are hindered from binding to the label conjugate simultaneously. The second epitope can be a fluor the fluroescence of which is quenched by the second antibody binding, or which may participate in an ancillary competitive binding reaction with a labeled form of the second epitope for binding to the second antibody. Various detectant systems are possible in such a system as described in the aforementioned patents. Related assay systems are described in U.S. Pat. Nos. 4,130,462 and 4,161,515 and in British Patent Spec. No. 1,560,852.

(j) Energy Transfer Labels

In this system, the label is one member of an energy transfer donor-acceptor pair and the binding partner is conjugated with the other of such pair. Thus, when the label conjugate is bound by binding partner, the energy expression of the donor component of the pair is altered by transferance to the acceptor component. Usually, the donor is a fluor and the acceptor is a quencher therefor, which quencher may or may not be a fluor as well. In such embodiment, the detectable signal is fluorescence, but other detectant systems are possible also. Such assay systems are described in U.S. Pat. Nos. 3,996,345; 4,174,384; and 4,199,559 and in British Patent Spec. No. 2,018,424.

(k) Other Labels

Other homogeneous specific binding assay systems described in the art which can be used in the present invention include the use of such labels as:

(i) nonenzymic catalysts, such as electron transfer agents (see U.S. Pat. No. 4,160,645);

(ii) nonenzymic chemiluminescers (see commonly owned, copending application Ser. No. 894,836 referred to above);

(iii) "channeling" labels (see British Patent Spec. No. 2,018,986);

(iv) "particle" labels (see British Patent Spec. No. 2,019,562); and (v) labeled liposome particles (see U.S. Pat. No. 4,193,983).

4. THE REAGENT LAYER(S)

Also provided is a method of preparing the reagent layer(s) as radiation diffusing and blocking layer o or the subbing layer, if the latter is used. The devices of the present invention can be made by any suitable technique, such as printing or spraying the reagent composition onto layer or by using any of the radiation diffusing and blocking layer or the subbing the known film forming techniques.

Where the reagent layer actually comprises multiple layers, such layers can, if desired, be maintained in laminar relationship by adhesives which permit fluid passage between layers. Ordinarly, however, it is not necessary to employ adhesive to adhere one reagent layer to another. In preparing integral analytical elements using film formers, the layer(s) can be preformed separately and laminated to form the overall element. The material of the film layer(s) can be a composition comprising a plasticizer and a polymer suitable to impart dimensional stability. Layers prepared in such a manner are typically coated from solution or dispersion onto a surface from which the dried layer can be physically stripped. However, a convenient method which can avoid problems of multiple stripping and lamination steps is to coat an initial layer on a stripping surface or a support, as desired, and thereafter to coat successive layers directly on those coated previously. Such coating can be accomplished by hand, using a blade coating device, or by machine, using techniques such as dip or bead coating. If machine coating techniques are used, it is often possible to coat adjacent layers simultaneously using hopper coating techniques well known in the preparation of light sensitive photographic films and papers.

Blush polymer layers can be used as the film layer material. The film is formed on a substrate by dissolving a polymer in a mixture of two liquids, one of which is of a lower boiling point and is a good solvent for the polymer and the other of which is of a higher boiling point and is a nonsolvent or at least a poor solvent for the polymer. Such a polymer solution is then coated on the substrate, and dried under controlled conditions. The lowr boiling solvent evaporates more readily and the coating becomes enriched in the liquid which is a poor solvent or nonsolvent. As evaporation proceeds, under proper conditions, the polymer forms as a porous layer. Many different polymers can be used, singly or in combination, for preparing porous blush polymer layers for use in this invention. Typical examples include polycarbonates, polyamides, polyurethanes and cellulose esters, such as cellulose acetate. For layers such as those containing a label conjugate or other reagent, a coating solution or dispersion including the matrix and incorporated active materials can be prepared, coated as discussed herein and dried to form a dimensionally stable layer.

The thickness of any reagent layer and its degree of permeability are widely variable and depend on actual usage. Dry thicknesses of from about 5 microns to about 100 microns have been convenient, although more widely varying thickness may be preferably in certain circumstances. For example, if comparatively large amounts of interactive material, e.g., polymeric materials like enzymes, are required, it may be desirable to prepare slightly thicker layers.

If can be advantageous to incorporate one or more surfactant materials, such as anionic and nonionic surfactant materials, in the reagent layer(s). They can, for example, enhance coatability of layer formulations and enhance the extent and range of wetting in layers that are not easily wetted by liquid samples in the absence of an aid such as a surfactant. It can also be desirable to include materials that can render nonactive in the analysis of choice, by chemical reaction or otherwise, materials potentially deleterious to such analysis.

Following are descriptions of some preferred approaches to preparation of the reagent layer(s):

(a) Multilayer Approach

This approach relates to a method for preparing the reagent layer of a homogeneous specific binding assay element for determining a ligand in or the ligand binding capacity of a liquid sample by incorporating a composition which includes a label conjugate, comprising a label component coupled to a ligand moiety or a specific binding analog thereof, and a reagent interreactive with the label conjugate. The reagent can comprise, for example, a specific binding partner for the ligand or a specific binding partner for the ligand and a component which is interreactive with the label conjugate to cleave the label component from the ligand moiety or specific binding analog thereof.

The reagents can be applied in respective solutions which are incapable of substantial interreaction during preparation of the test device and thus do not react prematurely. In a preferred embodiment, certain first reagents are incorporated with a layer using an aqueous dip. For the remaining reagents, a suitable organic solvent is used such as toluene, acetone, chloroform, methylene chloride, n-propanol and ethylene dichloride. This layer is set by allowing the organic solvent to evaporate.

An example of this preferred embodiment is a method for preparing a homogeneous specific binding assay device for determining a ligand in or the ligand binding capacity of a liquid sample by applying a composition which includes a $\beta$-galactosyl-umbelliferone-ligand or ligand analog conjugate, $\beta$-galactosidase, and antiserum to the ligand which method comprises (a) applying $\beta$-galactosidase and antiserum to the ligand in an aqueous liquid and (b) then applying $\beta$-galactosyl-umbelliferone-ligand or ligand analog conjugate in acetone.

(b) Multizone Reagent Layer

A multizone reagent layer is prepared by (a) incorporating a first or overlaying zone with some, but less than all, of the reagents of the specific binding assay system used, (b) incorporating a second or underlaying zone with the remaining reagents, (c) setting, such as by drying, the individual zones, and (d) fixing them into laminar relationship with one another.

The first layer and second layer each have a pair of opposite surfaces. One surface of the first layer is in laminar relationship with one surface of the second layer, sample being applied to the other surface of either of said layers. Reference to a laminar relationship connotes the ability of a fluid, whether liquid or gaseous, to pass between superposed surfaces of such layers. Such layers can be continguous or separated by intervening layers. Any intervening layer should not prevent passage between all layers.

(c) Freeze Drying Approach

This approach consists of a procedure to incorporate and prevent reaction between incompatible reagents in a single layer analytical element. For example, a first group of reagents is applied by freeze drying or at elevated temperature and the treated layer is set. The second group of reagents, containing any which will react under ambient conditions with the first group, are applied and the element is rapidly frozen. Freezing prevents premature reaction and the subsequent removal of water by freeze drying prevents premature reaction when the layer is brought back to room temperature.

In the preferred embodiment, one group of reagents can be added in aqueous solution to a layer and dried. The addition of a second group of reagents in aqueous solution is followed by rapid freezing and then freeze drying to remove water. This procedure allows the incorporation of and prevents the interaction between some reagents which are only water soluble. In addition, it avoids the use of organic solvents, certain of which may interact deleteriously with some reagents (e.g., enzymes).

The procedure permits formulation of elements utilizing homogeneous specific binding assay reagents in which all reagents are provided within a single layer element.

(d) Preformed Complex Approach

Competition between sample ligand and labeled ligand for binding to a binding partner (here exemplified by an antibody-"Ab") can be summarized by the equation:

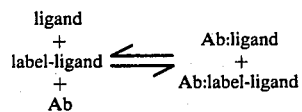

In the system illustrated above, the antibody and the label conjugate are kept separate until the introduction of the sample. This embodiment of the described invention makes use of the reverse reaction and reequilibration with the ligand as shown by the equation below:

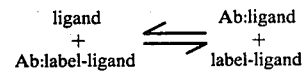

where the amount of displaced label conjugate is related to the sample ligand concentration. The advantage is that all reagent components can be combined in one incorporation medium to provide a system that requires only the addition of sample to be tested.

As such, this approach provides a method of preparing the reagent layer of a homogeneous specific binding assay device for determining a ligand in a liquid sample, which method comprises (a) forming a complex between a label conjugate, the conjugate comprising a label component coupled to the ligand or a specific binding analog thereof, and a specific binding partner for the ligand; and (b) applying the complex. In this method, forming the complex can comprise associating the label conjugate and specific binding partner therefor and allowing the conjugate, the binding partner and the complex to reach a state of equilibrium.

More particularly, the layers are prepared by incubating a given conjugate with its respective antisera for a short period, such as 15 minutes. Then, any additional reagents are added and the system allowed to incubate an additional period. The solution so formed is then allowed to set.

5. THE SUPPORT LAYER

As mentioned previously herein, the integral analytical elements include a support. The support can be opaque, translucent or transparent to light or other energy. A support of choice for any particular element will be selected independently of the intended mode of signal detection. Preferred supports include those of polystyrene or similar plastics.

6. MULTILAYER ELEMENT PREPARATION

Further in accordance with the invention there is provided a method for the preparation of a multilayer analytical element for the detection of a ligand in or the ligand binding capacity of a liquid sample of the type having a reagent layer incorporating reagents which are responsive to the ligand in or the ligand binding capacity of the sample to give a detectable response, a radiation diffusing and blocking layer, and a support layer, each such layer having opposed surfaces, which method comprises the steps of:

(1) fixing a surface of the support layer to a surface of a radiation diffusing and blocking layer which is
(a) impermeable to the ligand, reagents of the reagent layer, and products of their interreaction; and
(b) inert to the ligand, reagents of the reagent layer, and products of their interreaction; and
(2) fixing a surface of the reagent layer to the opposed surface of the radiation diffusing and blocking layer.

In one embodiment, fixing a surface of the support layer to a surface of the radiation diffusing and blocking layer comprises forming the radiation diffusing and blocking layer on the surface of the support layer. In another embodiment, fixing a surface of the support layer to a surface of the radiation diffusing and blocking layer comprises forming the radiation diffusing and blocking layer and, thereafter, fixing a surface of the radiation diffusing and blocking layer so formed to a surface of the support layer.

7. DETECTABLE RESPONSE

As previously noted, many of the recently devised homogeneous specific binding assay systems provide, or can be readily adapted to provide, a detectable response such as a color change, chemiluminescence, or fluorescence related to the presence or amount of the ligand under assay in the liquid sample.

The terms "detectable species" and similar terms as used herein, refer to atoms, chemical groups (i.e., a portion of a molecule) or chemical compounds that are themselves directly or indirectly detectable and the term "detectable response", and similar terms as used herein, refer to the detectable manifestation of the presence of such species. Examples are electromagnetic radiation signals such as fluorescence, phosphorescense, chemiluminescence, a change in light absorption, or reflectance in the visible spectrum thereby produing a visible color change, a change in light absorption or reflectance outside the visible range such as in the ultraviolet range or infrared range. As will be apparent to one skilled in the art the phrase "detectable response", as used herein, is intended in its broadest sense. In addition to electromagnetic radiation signals the term "detectable response" is also meant to include any observable change in a system parameter, such as a change in or appearance of a reactant, observable precipitation of any component in the test sample or a change in any other parameter, whether it be in the reagent system or the test sample. Such other detectable responses include electrochemical responses and calorimetric responses. Moreover, the detectable response is one which can be observed through the senses directly or by use of ancillary detection means, such as a spectrophotometer, ultraviolet light-sensing equipment, fluorometer, spectrofluorometer, and other similar sensing means. Desirably, such detectability can be conveniently imparted to the full amount of detectable species without affecting the amount of diffusible product resulting from the analyte interactions which are the basis of the intended analysis.

After the analytical result is obtained as a detectable change, it is measured, usually by passing the test element through a zone in which suitable apparatus for reflection, transmission or fluorescence photometry is provided. Such apparatus serves to direct a beam of energy, such as light. The light is then reflected from the element back to a detector. The analytical result is detected in a region of the element totally within the region in which such result is produced. Use of reflection spectrophometry can be advantageous in some situations as it effectively avoids optical interference from any residues, such as blood cells or urine sediment, which have been left on or in the layers of the element or from atypical urine colors. Conventional techniques of fluorescence spectrophotometry can also be employed. Generally, electromagnetic radiation in the range of from about 200 to about 900 nm has been found useful for such measurements, although any radiation to which the reagent layer(s) is permeable and which is capable of quantifying the product produced in the element can be used. Various calibration techniques can be used to provide a control for the analysis. As one example, a sample of a standard solution of the ligand under assay can be applied adjacent to the area where the drop of sample is placed in order to permit the use of differential measurements in the analysis.

EXAMPLES

The following examples describe experiments which were performed in developing the present invention. While they illustrate preferred embodiments, they are in no way to be interpreted as limiting the scope of the invention.

EXAMPLE I—Comparison of Model Systems

In order to evaluate the effect of the blocking layer of the invention, elements were prepared both with and without the described radiation diffusing and blocking layer between the reagent layer and support layer. The reagent layer in this model system is provided with a reagent solution which, itself, emits a detectable response, fluorescence. Therefore, this example encompasses a comparison which is not limited to any particular ligand.

Element Preparation

The elements of both types were prepared using support layers some of which were of a polyester and others of which were gel bond film, all having 0.5 centimeter (cm) by 1.0 cm dimensions. Devices A and B have the support layer between the radiation diffusing and blocking and reagent layers; device B having a multizone reagent layer. In device C the reagent layer is between the support and radiation diffusing and blocking layers. Device D has the radiation diffusing and blocking layer between the reagent and support layers, and is exemplary of the invention.

Device A was prepared by casting a reagent layer film of an agarose composition on one surface of the support layer and a $TiO_2$ pigmented composition on the other surface to form a radiation diffusing and blocking layer. The agarose composition was formulated as follows:

| Component | Quantity |
|---|---|
| Agarose | 1.5 grams (g) |
| Triton X-100 (10% w/v) | 500.0 microliters |

-continued

| Component | Quantity |
| --- | --- |
| 1 M (molar) Bicine (pH 8.3) | 10.0 liters |
| H₂O | 40.0 milliliters |

Triton is a trademark for a line of synthetic organic surface-active agents sold by Rohm & Hass, Philadelphia, PA. Bicine is N,N-bix-(2-hydroxyethyl)-glycine.

The TiO₂ pigmented composition was formulated as follows:

| Component | Quantity |
| --- | --- |
| TiO₂ | 2.5 g |
| PVP | 2.5 g |
| Chloroform | 44.5 g |
| Dioctylphalate | 0.5 g |

The preparation of device B was identical to that of device A, as described above, with the addition that a polyvinylpyrrolidone (PVP) composition was cast as a film onto the surface of the agarose film opposite from the surface in contact with the support layer. The PVP composition formed a film which combined with the agarose film to form a multizone reagent layer and was formulated as follows:

| Component | Quantity |
| --- | --- |
| PVP | 5.0 g |
| Chloroform | 45.0 g |

Device C was prepared by casting a reagent layer film of an agarose composition on one surface of the support layer. The agarose composition was identical to that used in Devices A and B. The same TiO₂ composition used for Devices A and B was then used to cast a film on the surface of the agarose film opposite from the surface in contact with the support layer.

Device D was prepared by casting a TiO₂ pigmented composition, identical to that used in the other devices, onto a support layer to form a radiation diffusing and blocking layer and, then, casting an agarose composition, identical to that used in the other devices, onto the surface of the agarose layer opposite that in contact with the support layer.

In addition, 0.5×1.0 cm pieces of Whatman 31 ET filter paper (Whatman, Inc., Clifton, N.J. 07014) and reflective Mylar polyester (3M Company, St. Paul, MN 55144) were laminated together to form Device E. No reagent was present in the devices formed.

Analytical Procedure

The devices prepared as described above were each inserted into a mechanical holder suitable for horizontal positioning of the device in a fluorometer. A 30 microliter ($\mu$L) drop of a 7-hydroxycoumarin-3-carboxanilide (HCC) aqueous solutions was placed on each device just prior to placing that device into the fluorometer. Each of the HCC solutions used was in the range from 0.2 to 2.0 micromolar ($\mu$M) concentrations.

The fluorometer had been adjusted to provide an excitation light source of 405 nanometers (nm) wavelength, which struck the surface of the element at a 90° angle from the plane of the surface, and to detect light emitted at a wavelength of 450 nm. A front face measurement of fluorescence was made at a 90° angle from the plane of the element surface. The fluorescence of each sample was then measured.

Results

The range (R) and the signal to background (S/B) for each HCC sample were determined, respectively, using expressions 1 and 2:

(1) $R = F_m - F_b$    (2) $S/B = F_m/F_b$ where $F_b$ and $F_m$ are the fluorescence signal for a blank and an HCC solution, respectively.

Figure 2:
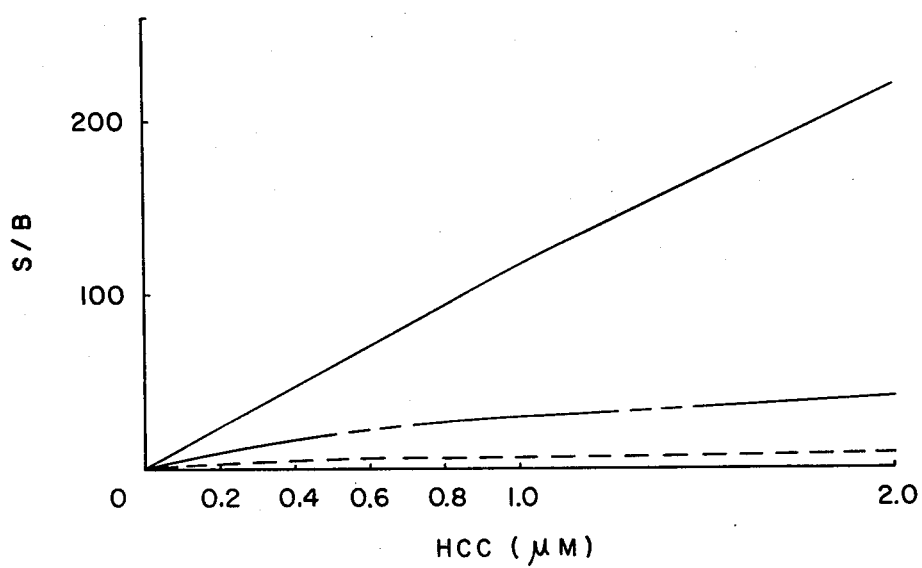

The data obtained using Devices A and B is represented in both FIGS. 1 and 2 by the curve drawn in dashed line. The data obtained using Devices C and D is represented in both FIGS. 1 and 2 by the curve drawn in solid line. The data obtained using Device E is represented in both FIGS. 1 and 2 by the curve drawn in phantom line.

FIG. 1 illustrates a plot of the range as a function of the HCC concentration for each system. Aside from Whatman 31ET (Device E), two distinct responses are observed for the TiO₂ systems. The preparations with the TiO₂ beneath the support (Devices A and B), whether gel bond or polyester, show a lower range than those with the TiO₂ on top of the support (Devices C and D), whether gel bond or polyester, in contact with the HCC solutions. Whatman 31ET (Device E) shows a better range than the TiO₂ systems.

The same phenomenon between devices A and B on the one hand and devices C and D on the other, is observed when the signal/background (S/B) ratios are plotted against HCC concentrations as illustrated in FIG. 2. The preparations with the TiO₂ on top of the support, shielding the layer receiving the HCC solutions, show large S/B ratios. Those with TiO₂ beneath the support show small ratios and Whatman 31ET (Device E) is intermediate.

EXAMPLE II—Substrate-Labeled Fluorescent Immunoassay Element for Theophylline.

Theophylline [1,3-dimethylxanthine, c.f. *The Merck Index*, 9th ed., p. 1196 (1976)] is a drug useful in the management of asthma. In most patients, the therapeutic range of serum concentrations lies between 10 and 20 micrograms per milliliter ($\mu$g/ml) whereas toxicity almost invariably appears at blood levels over 35 $\mu$g/ml.

Figure 3:
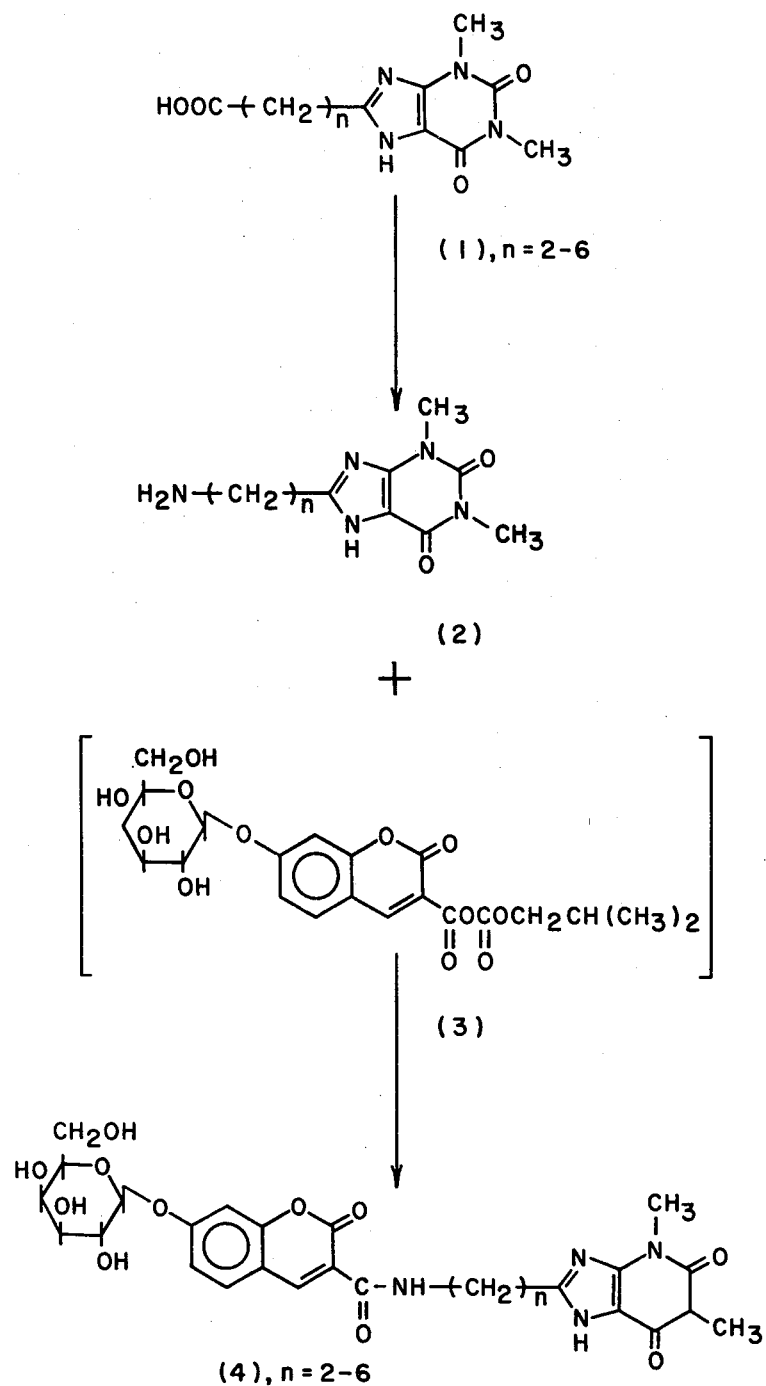
FIG. 3 is a representation of the procedure used to prepare the conjugate used in EXAMPLE II.

Conjugate Preparation $\beta$-galactosyl-umbelliferone-labeled theophylline ($\beta$-GUT) conjugates were prepared according to the reaction scheme shown in FIG. 3. This synthetic route is exemplified by the following method of preparing 8-[3-(7-$\beta$-galactosylcoumarin-3-carboxamido)propyl] theophylline (4), n=3.

8-(3-Aminopropyl)theophylline (2)

A mixture of 2.66 g (0.01 mol) of 8-(3-carboxypropyl)theophylline (1) [Cook et al, *Res. Commun. Chem. Path. Pharmacol.* 13(3):497–505 (1976)], 20 ml of chloroform, and 3 ml of concentrated sulfuric acid was stirred at 50° C. under an argon atmosphere. To this was added 1.3 g of solid sodium azide protion-wise over a 90 minute period [cf. Organic Reactions 47:28 (1967)]. The reaction was cooled and the solvent removed under reduced pressure. The residue was combined with enough sodium bicarbonate solution to bring the pH to 7.5. Ten grams of Celite (Fisher Scientific Co., Pittsburgh, Pennsylvania) was added and the water evaporated. Celite is a trademark for certain diatomaceous earth products. The impregnated Celite was placed atop a column of 200 g of silica gel (E. Merck Co., Darmstadt, West Germany) made up in 9:1 (v:v) ethanol-1 molar aqueous triethylammonium bicarbonate. The column was eluted with this solvent and 15 ml fractions were collected. Fractions 171 to 225 were combined and evaporated to give 500 mg of a white powder. This substance was rechromatographed on a column of CM-Sephadex, ammonium form (Pharmacia Fine Chemicals, Piscataway, New Jersey, USA), eluting with 0.5 molar ammonium bicarbonate. The bed volume was 3 cm by 50 cm; and 10 ml fractions were collected. Fractions 65 to 110 were combined and evaporated to give 250 mg of a white solid. It was taken up in dilute hydrochloric acid, then reevaporated.

The residue was recrystallized from methanol to give 90 mg (3% yield) of the hydrochloric acid salt of (2) as pale tan needles that did not melt below 300° C.

Analysis: Calculated for $C_{10}H_{16}N_5C1O_2$: C, 43.88; H, 5.89; N, 25.59. Found: C, 43.77; H, 5.88; N, 25.46. Infrared Spectrum (KCl): 1695 $cm^{-1}$ and 1655 $cm^{-1}$ (amide carbonyls).

8-[2-(7-β-galactosylcoumarin-3-carboxamide)-propyl]-theophylline (4).

A reaction mixture was prepared containing 24 g of potassium hydroxide, 80 ml of water, 240 ml of methanol and 20 g (0.035 mmol) of ethyl 7-β-galactosyl-coumarin-3-carboxylate [Burd et al, *Clin. Chem.* 23: 1402 (1977)]. The reaction was stirred at 50° C. for 15 hours. When cool, the methanol was removed under reduced pressure. The concentrated aqueous solution was acidifed to pH 2.0 with concentrated hydrochloric acid. The white precipitate was collected, washed with cold water, and recrystallized from hot water. The crystals were collected, washed with acetone, and dried at 80° C. for 1 hour. This gave 12 g of 7-β-galactosyl-coumarin-3-carboxylic acid as white crystals, mp 250°–255° C.

A mixture of 1.45 g (0.004 mol) of 7-β-galactosyl-coumarin-3-carboxylic acid, 404 mg (0.004 mol) of triethylamine, and 40 ml of dry dimethyl formamide (DMF) was cooled at −10° C. while stirring under argon. To this was added 546 mg (0.004 mol) of isobutyl chloroformate (Aldrich Chemical Co., Milwaukee, Wisconsin) to form the mixed anhydride (3). Ten minutes later, an additional 404 mg of triethylamine and 949 mg (0.004 mol) of 8-(3-aminipropyl)theophylline (2) was added to the flask. After stirring for 30 minutes at −10° C., the reaction was allowed to warm to room temperature. It was combined with 10 g of silica gel and the DMF removed under high vacuum. The impregnated silica gel was placed atop a column of 170 g of silica gel and the column eluted with anhydrous ethanol and collecting 15 ml fractions. Fractions 41 to 475 were combined and evaporated to give 545 mg of a yellow solid. It was dissolved in water, filtered, and concentrated to a 20 ml volume. A small amount of precipitate formed and was discarded. The filtrate was chromatographed on a 2.5 cm by 57 cm column of Sephadex LH-20 gel (Pharmacia Fine Chemicals, Piscataway, New Jersey), eluting with water and collecting 15 ml fractions. Sephadex is a trade name for a hydrophilic, insoluble molecular-sieve chromatographic medium, made by cross-linking dextran. Fractions 18 to 23 were combined, evaporated, and residue recrystallized from water to give 55 mg (2% yield) of the label conjugate (4) as a light yellow solid, mp 190°–192° C.

Analysis: Calculated for $C_{26}H_{29}N_5O_{11}$: C, 53.15; H, 4.98; N, 11.92. Found: C, 52.65; H, 5.01; N, 11.80.

The above-described synthesis of the β-galactosyl-coumarin-theophylline conjugate (4), n=3, can be modified to yield label conjugates wherein n=2 through 6 by replacing the starting material 8-(3-carboxypropyl)-theophylline (1), n=3, with the appropriate 8-(ω-carboxyalkyl)theophylline as follows:

| n | Alkylene |
|---|----------|
| 2 | ethylene |
| 4 | butylene |
| 5 | pentylene |
| 6 | hexylene |

Antiserum Preparation

Antiserum was collected from rabbits immunized with a theophylline immunogen conjugate prepared as described by Cook et al. *Res. Comm. Chem. Path. Pharmacol.* 13:497–505 (1976).

Element Preparation

Figure 4:
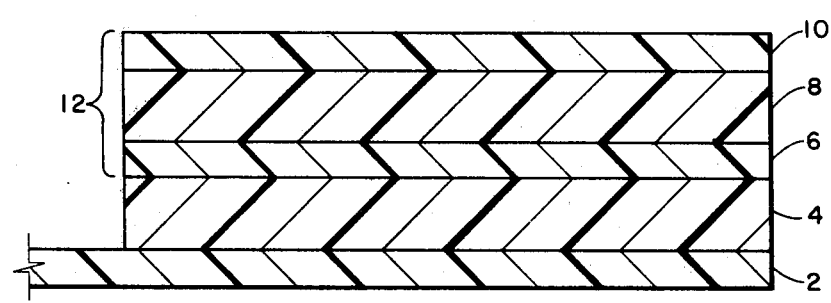
FIG. 4 is a cross-section view of a theophylline analytical element prepared as described in Example II.

The element prepared for use in these experiments had the configuration shown in FIG. 4. The support layer 2 is of polystyrene. The impermeable radiation diffusing and blocking layer 4 is of a composition having the following formulation:

| | |
|---|---|
| styrene/maleic anhydride (50/50 copolymer, MW 50,000) | 10 g |
| polyethylene glycol (MW 1,000) | 6 g |
| titanium dioxide | 10 g |
| acetone | 34 g |

This composition was cast onto the polystyrene support layer 2 to a wet thickness of 0.02 inches and allowed to dry at room temperature.

A gelatin subbing layer 6 adheres to the surface of the impermeable radiation diffusing and blocking layer 4 and forms one zone of the multizone reagent layer 12. The subbing layer is of a composition having the following formulation:

| | |
|---|---|
| gelatin | 5 g |
| 0.1 M bicine buffer (pH 11.1) | 45 g |

This composition was cast onto layer 4 to a wet thickness of 0.005 inches and dried at 37° Centigrade (C).

An antibody and enzyme containing layer 8 was prepared of a composition having the following formulation:

| | |
|---|---|
| 4% (w/v) agarose LGT in 0.8 M bicine buffer (pH 8.5) | 1.5 ml |
| 10% Triton X-100 (w/v) | 30 μl |
| 1 M bicine, 0.1 M MgCl₂, pH 8.5 | 300 μl |
| antisera to theophylline | 464 μl |
| β-galactosidase (177 U/ml) | 430 μl |
| double distilled water | 276 μl |

Agarose LGT is an agarose material having a low grilling temperature of below 40° C. and is sold by the Research Products Division of Miles Laboratories, Inc., P.O. Box 2000, Elkhart, Indiana 46515. This composition was cast onto layer 6 to a wet thickness of 0.02 inches and dried at 37° C. It is the intermediate zone of the multizone reagent layer 12.

A conjugate containing layer 10 was prepared of a composition having the following formulation:

| | |
|---|---|
| β-GUT conjugate | 69.2 μl |
| 6% (w/w) PVP (MW 360,000) in CHCl$_3$ (1.93 ml) | 2.90 g |
| Triton X-100 | 5 μl |

This composition was cast onto layer 8 to a wet thickness of 0.005 inches and dried at room temperature. It is the uppermost zone of the multizone reagent layer 12. The exposed upper surface of layer 10 is the surface to which sample is applied and from which readings are taken.

Analytical Procedure 35 microliter (μl) aliquots of drug solution were pipetted onto the exposed surface of the analytical elements prepared as described above.

The fluorescence generated at room temperature was measured for a duration of five minutes in a fluorometer equipped with a mechanical holder suitable for horizontally positioning the analytical element. The fluorometer had been adjusted to provide an excitation light source at 405 nm, which struck the surface at 90° and to detect light emitted at a wavelength of 450 nm. A front face measurement of fluorescence was made at a 90° angle from the pad.

The concentration ranges assayed were as follows:

| RANGE | THEOPHYLLINE |
|---|---|
| Therapeutic Range | 10–20 μg/ml |
| Dose Response Range Checked | 0–41 μg/ml |

The dose response range checked covers the therapeutic range.

Results

Figure 5:
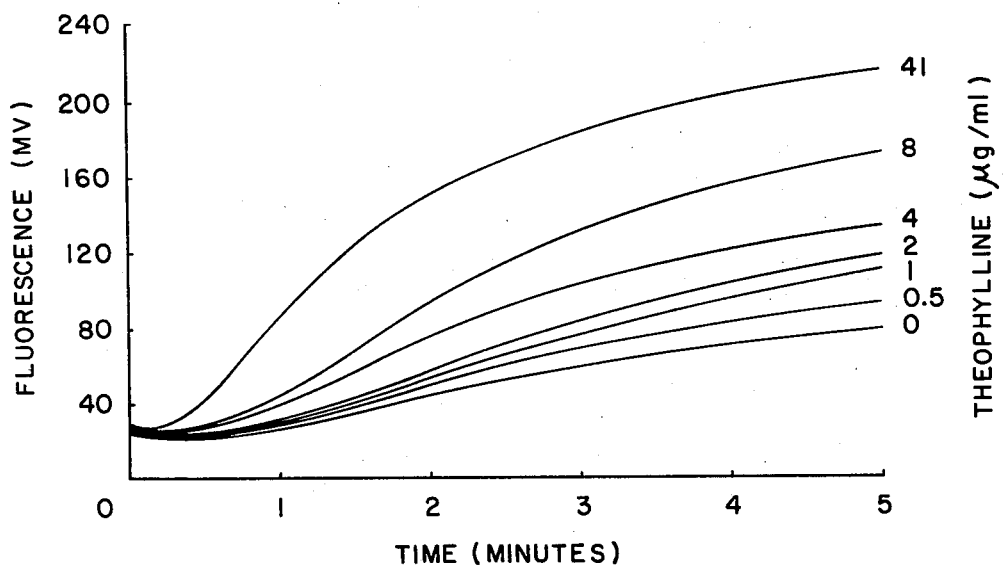
FIGS. 5-6 are graphical representation of data obtained from the experiments described in Example II.
Figure 6:
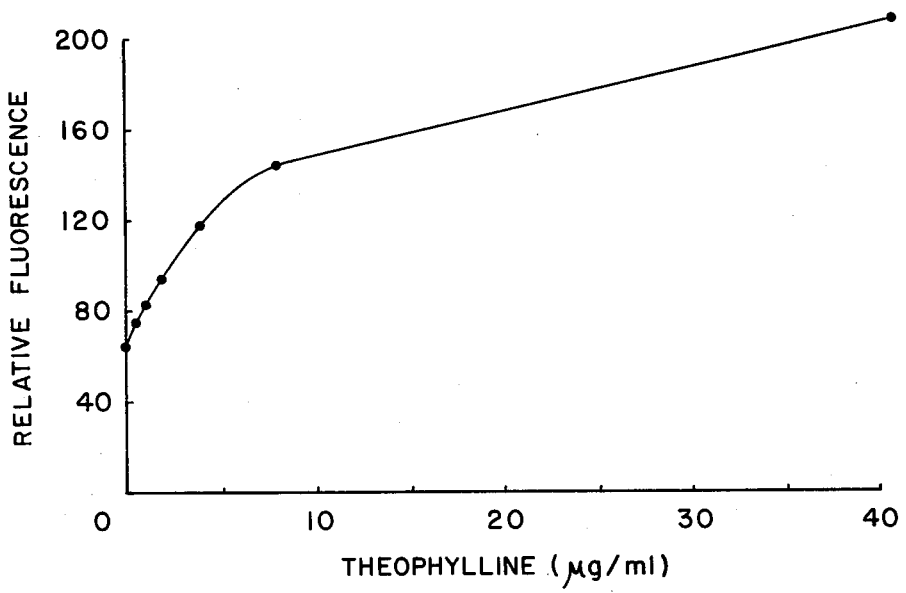

The data obtained by the above-described procedure is graphically illustrated by FIG. 5. The ordinate units are expressed in terms of millivolts (mv). A millivolt is one thousanth of a volt. A dose response curve, FIG. 6, was prepared from the data shown in FIG. 6 at the three (3) minute point.

Conclusion

The resultant data show that integral analytical elements, prepared according to the invention provide quantitatively detectable signals which are responsive to the concentration ranges of the theophylline present. Increasing concentrations of theophylline results in a drug dependent increase in fluorescence of the respective analytical elements.

What is claimed is:

1. In a multilayer analytical element for detecting a ligand in or the ligand binding capacity of a liquid sample of the type having a reagent layer incorporating reagents which are responsive to the ligand in or the ligand binding capacity of the sample to give a detectable response, a radiation diffusing and blocking layer, and a support layer, the improvement wherein the radiation diffusing and blocking layer is (a) interposed between the reagent layer and the support; (b) impermeable to the ligand, reagents present in the reagent layer, and products of their interreaction; and (c) inert to the ligand, reagents present in the present layer, and products of their interreaction.

2. The multilayer analytical element of claim 1 wherein the radiation diffusing and blocking layer is opaque, relatively thin and contains a white or light color pigment.

3. The multilayer analytical element of claim 2 wherein the pigment is titanium dioxide.

4. The multilayer analytical element of claim 2 where the pigment is barium sulfate.

5. The multilayer analytical element of claim 2 wherein the pigment is zinc oxide.

6. The multilayer analytical element of claim 2 wherein the pigment is magnesium oxide.

7. The multilayer analytical element of claim 2 wherein the pigment is zirconium dioxide.

8. The multilayer analytical element of claim 2 wherein the radiation diffusing and blocking layer constitutes an anhydride resin.

9. The multilayer analytical element of claim 2 wherein the radiation diffusing and blocking layer is between 0.0002 and 0.02 inches in thickness.

10. The multilayer analytical element of claim 2 wherein the pigment is uniformily distributed throughout the radiation diffusing and blocking layer.

11. The multilayer analytical element of claim 1 wherein the reagent layer comprises reagents for a homogeneous specific binding assay system which produces a detectable response that is a function of the presence of the ligand in or the ligand binding capacity of the sample.

12. The multilayer analytical element of claim 11 wherein the homogeneous specific binding assay system includes a label which participates in an enzymatic reaction.

13. The multilayer analytical element of claim 12 wherein the label is a substrate for an enzyme.

14. The multilayer analytical element of claim 13 wherein the enzyme is capable of acting on the substrate label to produce a detectable product.

15. The multilayer analytical element of claim 12 wherein the label is a prosthetic group of an enzyme.

16. The multilayer analytical element of claim 15 wherein the prosthetic group is capable of combining with an apoenzyme to form the enzyme.

17. The multilayer analytical element of claim 12 wherein the label is an enzyme.

18. The multilayer analytical element of claim 1 wherein the reagent layer comprises:
a reagent composition including
(i) an antibody which binds the ligand,
(ii) a conjugate of the ligand or a binding analog thereof, and a label, and
(iii) a detectant system which interacts with the label to produce a detectable response that is different when the label conjugate is bound by the antibody compared to when it is not so bound,
whereby the detectable response is a function of the presence of the ligand in the liquid sample.

19. The multilayer analytical element of claim 18 wherein the detectant system involves an enzymatic chemical reaction in which the label is a participant.

20. The multilayer analytical element of claim 19 wherein the label is a substrate for an enzyme and wherein the detectant system comprises the enzyme.

21. The multilayer analytical element of claim 19 wherein the label is a prosthetic group of an enzyme and the detectant system comprises an apoenzyme which combines with the prosthetic group to form the enzyme.

22. The multilayer analytical element of claim 21 wherein the detectant system additionally comprises an indicator for the activity of the enzyme.

23. The multilayer analytical element of claim 21 wherein the label is flavin adenine dinucleotide and the apoenzyme is apoglucose oxidase.

24. The multilayer analytical element of claim 21 wherein the detectant system additionally comprises an indicator for glucose oxidase activity.

25. The multilayer analytical element of claim 24 wherein the indicator comprises glucose, peroxiddase, and a substance which produces a chromogenic response to hydrogen peroxide.

26. The multilayer analytical element of claim 19 wherein the label is an enzyme and the detectant system comprises an indicator for the activity of the enzyme.

27. In a multilayer analytical element for detecting a ligand in or the ligand binding capacity of a liquid sample of the type having a reagent layer incorporating reagents which are responsive to the ligand in or the ligand binding capacity of the sample to give a detectable response, a radiation diffusing and blocking layer, and a support layer, the improvement wherein:
  (1) the reagent layer comprises
    (a) reagents for a homogeneous specific binding assay system which produces a detectable response that is a function of the presence of the ligand in or the ligand binding capacity of the sample; and
    (b) a solid carrier incorporated with the reagents; and
  (2) the radiation diffusing and blocking layer comprises a pigment incorporated into an anhydride resin, which layer is:
    (a) interposed between the reagent layer and the support layer;
    (b) impermeable to the ligand, reagents of the reagent layer, and products of their interreaction; and
    (c) inert to the ligand, reagents of the reagent layer, and products of their interreaction.

28. A method for the preparation of a multilayer analytical element for the detection of a ligand in or the ligand binding capacity of a liquid sample of the type having a reagent layer incorporating reagents which are responsive to the ligand in or the ligand binding capacity of the sample to give a detectable response, a radiation diffusing and blocking layer, and a support layer, each such layer having opposed surfaces, which method comprises the steps of:
  (1) fixing a surface of the support layer to a surface of a radiation diffusing and blocking layer which is
    (a) impermeable to the ligand, reagents of the reagent layer, and products of their interreaction; and
    (b) inert to the ligand, reagents of the reagent layer, and products of their interreaction; and
  (2) fixing a surface of the reagent layer to the opposed surface of the radiation diffusing and blocking layer.

29. A method for detecting a ligand in or the ligand binding capacity of a liquid sample which method comprises contacting the sample with a multilayer analytical element of the type having a reagent layer incorporating reagents which are responsive to the ligand in or the ligand binding capacity of the sample to give a detectable response, a radiation diffusing and blocking layer, and a support layer, the improvement wherein the radiation diffusing and blocking layer is
  (a) interposed between the reagent layer and the support layer;
  (b) impermeable to the ligand, reagents of the reagent layer, and products of their interreaction; and
  (c) inert to the ligand, reagents of the reagent layer, and products of their interreaction.

* * * * *